(12) United States Patent
Kato et al.

(10) Patent No.: US 8,067,036 B2
(45) Date of Patent: Nov. 29, 2011

(54) GNETUM EXTRACT

(75) Inventors: Eishin Kato, Fukui (JP); Shinya Hosoda, Fukui (JP)

(73) Assignee: Hosoda SHC Inc., Fukui (JP)

( * ) Notice: Subject to any disclaimer, the term of this patent is extended or adjusted under 35 U.S.C. 154(b) by 477 days.

(21) Appl. No.: 10/570,485

(22) PCT Filed: Sep. 13, 2005

(86) PCT No.: PCT/JP2005/016824
§ 371 (c)(1),
(2), (4) Date: Mar. 3, 2006

(87) PCT Pub. No.: WO2006/030771
PCT Pub. Date: Mar. 23, 2006

(65) Prior Publication Data
US 2008/0274218 A1    Nov. 6, 2008

(30) Foreign Application Priority Data

Sep. 14, 2004  (JP) ................................. 2004-266457
Feb. 21, 2005  (JP) ................................. 2005-043995
Apr. 4, 2005   (JP) ................................. 2005-107123

(51) Int. Cl.
*A61K 36/00*    (2006.01)
*A23L 1/36*     (2006.01)
*A23L 1/221*    (2006.01)
*A23L 3/015*    (2006.01)

(52) U.S. Cl. .......... 424/725; 424/776; 426/44; 426/655; 426/650

(58) Field of Classification Search .................. None
See application file for complete search history.

(56) References Cited

FOREIGN PATENT DOCUMENTS

| CN | 1732999 A | 2/2006 |
| JP | 11-60450 | 3/1999 |
| JP | 11060450 A * | 3/1999 |
| JP | 2002-80372 | 3/2002 |
| JP | 2005-23000 | 1/2005 |

OTHER PUBLICATIONS

Boralle et al (Oligostibenoids from *Gnetum venosum*, Phytochemistry, 34 (5): 1403-1407, 1993.*
Conte, Storage globulins in Gnetopsida. 1. Recognition of legumin-like proteins. Giornale Botanico Italiano, (1994) vol. 128, No. 5, pp. 839-843.*
Berry, Cyclopropene fatty acids in *Gnetum gnemon* (L.) seeds and leaves, Journal of the Science of Food and Agriculture, (1980) vol. 31, No. 7, pp. 657-662.*
Iliya et al, Stilbene derivatives from two species of Gnetaceae, Chem. Pharm. Bull. 50 (6) 796-801 (2002).*
Qi, Optimum for extraction processing of stilbene glucoside from Polygonum multiflorum, Zhongcaoyao (2002), 33(7), 609-611.*
I. Iliya, et al.; "Three New Trimeric Stilbenes from *Gnetum gnemon*;" *Chem. Phar. Bull.*; vol. 51; No. 1; 2003; pp. 85-88.
E.U. Isong, et al.; "Nutritional and phytogeriatological studies of three varieties of *Gnetum africanum* ('afang');" *Food Chemistry*; vol. 64; 1999; pp. 489-493.
S.K. Berry; "Cyclopropene Fatty Acids in *Gnetum gnemon* (L.) Seeds and Leaves;" *J. Sci. Food Agric.*; vol. 31; 1980; pp. 657-662.
Manner H. I. et al., "*Gnetum gnemon* (gnetum)," Species Profiles for Pacific Island Agroforestry, Ver. I.I, Apr. 2006, pp. 1-9.
Supplementary European Search Report dated Feb. 25, 2010, issued on the European Patent Application No. 05783166.1.

* cited by examiner

*Primary Examiner* — Qiuwen Mi
(74) *Attorney, Agent, or Firm* — Edwards Angell Palmer & Dodge LLP

(57) ABSTRACT

*Gnetum* extract which can be obtained from *Gnetum* fruit or *Gnetum* seeds that provide antimicrobial action and antioxidative effect (radical scavenging action) without carrying out special operation. The relevant *Gnetum* extract has various physiological (pharmacological) actions and can be used as active ingredients of foods, nourishments (nutritional supplements), medicines, cosmetics, etc. In addition, *Gnetum* extract is obtained by immersing sliced or ground *Gnetum* fruit or *Gnetum* seeds in water or water containing organic solvent and aging.

12 Claims, 1 Drawing Sheet

GNETUM EXTRACT

TECHNICAL FIELD

The present invention relates to liquid with high concentrations or powder (hereinafter called the "*Gnetum* extract") containing new material extracted from *Gnetum* fruit (seeds and/or pericarps).

And *Gnetum* extract according to the present invention can be expected for applications as material for foods, seasonings, nourishments, medicines, cosmetics, etc.

The present *Gnetum* extract provides antioxidizing effect that suppresses oxidation of lipids in foods and protects oxidative injury of organisms, thyrosinase inhibitory action, cyclooxynase inhibitory action, lipoxigenase inhibitory action, acetylcholinesterase inhibitory action, protein kinase C-inhibitory action, topoisomerase II-inhibitory action, ultraviolet-protective action, whitening action, anti-inflammatory action, immunoregulatory action, hair-growing action, and outstanding antibacterial and deodorizing action against nasty smell and offensive smell caused by proliferation of harmful microorganisms.

By the way, in the following description, "parts" and "%" that indicate the compounding unit mean the regular "parts by mass" and "% by mass" unless otherwise specified.

In addition, "extract" means the extractable matter obtained from the portion eaten (for example, flesh of fruit and dried bonito) and the "extracted material" means the extractable matter obtained from the portion usually not eaten (for example, pericarp, etc.). In the case of *Gnetum* according to the present invention, it is primarily extracted from the portion usually eaten and therefore called "extract."

BACKGROUND OF TECHNOLOGY

The present application has 1) Japanese Patent Application 2004-266457 (filing date: Sep. 14, 2004) "*Gnetum* seed extract"; 2) Japanese Patent Application 2005-43995 (filing date: Feb. 21, 2005) "Manufacturing process of *Gnetum* seed extract"; and 3) Japanese Patent Application 2005-107123 (filing date: Apr. 4, 2005) as the basis of priority.

With respect to the use conditions of *Gnetum* (botanical name: *Gnetum gnemon* L.), in Indonesia, young leaves, flowers and unripe fruit are merely consumed as vegetables. And seeds are ground, dried, and fried to serve as crackers (emping), and the use of *Gnetum* as functional foods in which the physiological action is positively utilized has not yet been carried out.

In addition, as an example of physiological functions of plant of the genus *Gnetum* in Gnetaceae family, only the hair-growing action of Mai ma teng (botanical name: *Gnetum montanum*) is disclosed (Japanese Patent Laid-Open Publication Hei 11-60450) and nothing is found for physiological functions of *Gnetum* seed.

By the way, a technique to obtain an antibacterial agent (resveratrol polymer) from extracts produced by extraction of the portion of plants of Gnetaceae with solvent was set forth in the prior application (Japanese Patent Laid-Open Publication 2005-23000) in Japan which was published between the above-mentioned priority-based applications 1) and 2).

That is, the prior invention is a patent concerning an antibacterial agent with resveratrol polymer that can be obtained by extraction and separation from the plant body of Gnetaceae and shows antibacterial action against drug resistance bacteria (methicillin-resistant *Staphylococcus aureus* and vancomycin-resistant *Enterococcus*). The patent describes also its food products and disinfectants, and antioxidative effect and anti-inflammatory effect.

Although the seeds are mentioned illustratively as the plant body of Gnetaceae and the use of root is mentioned to be preferable as the portion of plant body, nothing is described anywhere that it is preferable to positively use seeds. In addition, nothing is described about antimicrobial action (bacteriostatic action) against bacteria, yeasts, and fungi concerned with food putrefaction and secondary contamination.

On the other hand, to obtain extract (material highly contained extractable matter) from the root of plant body means removal of the plant body itself, and it is difficult to secure the amount and collection of roots is troublesome and inefficient as compared with collection of seeds, and furthermore, the plant body can be damaged and its energy can be spoiled.

DISCLOSURE OF THE INVENTION

An object (problem to be solved) of the present invention is to provide new *Gnetum* extract, which has various actions with good productivity without losing physiological action (pharmacological action) substances, with good productivity in view of the above.

The present invention encompasses *Gnetum* extract comprising high concentration liquid or powder containing new material extracted from *Gnetum* fruit (*Gnetum* seeds and/or pericarps) as one invention and also encompasses a group of inventions which has technological relationship containing special technological characteristics same as or corresponding to the *Gnetum* extract.

That is, the present invention other than *Gnetum* extract relates to material, containing *Gnetum* extract, which is in the stage before processing (converting) into *Gnetum* extract which contains the same or similar medicinal constituents (physiological constituents) and which can be utilized for foods with unconverted conditions, and further, foods, nourishments, seasonings, cosmetics, medicines, etc. to which material containing *Gnetum* extract is added as functional ingredients (antioxidative agent, antimicrobial agent, perfume, and other medicinal constituents and physiological constituents), and furthermore, a method of manufacturing *Gnetum* extract.

*Gnetum* (botanical name: *Gnetum gnemon* L.; English name: *Gnemon* tree; Indonesian name: Melinjo or Belinjo) is a plant of Gnetaceae, and popularly cultivated in Southeast Asia and used as food by boiling and roasting. The fruit (seed) which is used in the present invention, for example, contains 50% starch and 11% protein.

*Gnetum* fruit has a cross-sectional structure as shown in FIG. 1.

*Gnetum* fruit comprises pericarp (epicarp) 12, seed coat (endocarp) 14, thin skin (seed coat) 16, and embryo/albumen 18, and in general, in fruit, no juicy pulp (mesocarp) exists between the epicarp and the endocarp. Now, assume that the *Gnetum* seed comprises the endocarp 14, the thin skin 16, and the embryo/albumen (endosperm) 18. And the size of fruit is, in general, about 1.5 to 3 cm in major axis, about 1 to 2 cm in minor axis, and about 0.5 to 1 mm in epicarp wall thickness.

Seed can be used as material (material for extraction) under nondestructive state (including raw and dry) as it is but from the viewpoint of extraction efficiency, dried material (dry seed), heat-dried material and emping are sliced (chopped) or crushed (medium-ground) in slicer or crusher to have raw material.

Now, the "dried material" is the *Gnetum* fruit dried in the sun or in dryer (within 60° C.), while the "heat-dried material" is the *Gnetum* fruit dried at not higher than 100° C. without converting starch in seed into alpha-starch.

In addition, "emping" is produced by heating *Gnetum* seeds at not less than 100° C. to convert starch inside the seeds into alpha-starch, removing the seed coat from them, and flattening elastic endosperm made into alpha-starch, which is dried in shade. Prior to consumption, it is fried in oil or roasted.

Furthermore, where higher sophisticated physiological action is wanted for the extract (extractable material), the kernel removed pericarp and seed coat from the seed, that is, embryo/albumen (endosperm), is preferable. In this case, the *Gnetum* extract extracted and prepared from the removed pericarp and/or seed coat only by the method according to the present invention is also encompassed in the technical scope of the present invention.

In order to obtain *Gnetum* extract according to the present invention, the solvent for extraction shall be water and/or organic solvents.

Examples of organic solvents include 1) methanol, ethanol, 1-propanol, 2-propanol, 1-butanol, ethylene glycol, propylene glycol, glycerol and other alcohols (including diols and triols); 2) diethyl ether, Cellosolve, dioxane, tetrahydrofuran, and other ethers (including cyclic ethers); 3) methyl acetate, ethyl acetate, Cellosolve acetate, and other esters; 4) ketones such as acetone, acetic acid, glacial acetic acid, propionic acid, and other organic acids which are liquids at room temperature; 5) ethylene diamine, pyridine, monomethanol amine, and other amines; and furthermore, 6) hexane, cyclohexane, heptane, benzene, toluene, xylene, and other hydrocarbons (including aliphatic, alicyclic, and aromatic hydrocarbons); and 7) methylene chloride, chloroform, carbon tetrachloride, 1,2-dichloethane, dichloroethylene, trichloroethylene, and other halocarbons.

In the present invention, as an extractant, of the above-mentioned solvents, aqueous extractants comprising water and polar organic solvent are preferable. Among the above-mentioned organic solvents, the examples of the polar organic solvents used for the aqueous extractant include methanol, ethanol, propanol, butanol, and other lower alcohols, ethers such as diethyl ether, methyl acetate, ethyl acetate, and other esters, ketones such as acetone, which can be freely miscible with water, and acetic acid, glacial acetic acid, propionic acid, and other organic acids which are liquids at room temperature can be suitably used. Among these, in the case that the uses of *Gnetum* extract are foods and nourishments which the people directly eat and drink, solvents with high allowable residual concentration (for example, ethanol) are preferable since additional purification is not required.

Now, vodka, Japanese shouchu, whisky, gin, and other distilled liquors, and furthermore, Japanese sake, wine, and other alcoholic beverages made by fermentation can be substituted for the aqueous ethanol solution, and in such case, the use of *Gnetum* as fruit liquor (*Gnetum* liquor) becomes possible. In addition, in place of acetic acid, rice vinegar, apple-cider vinegar, and other brewed vinegars can be used, and in such case, the use of *Gnetum* as healthy vinegar (*Gnetum* vinegar) becomes available. In the case that these sprituous liquors, brewed liquors, or brewed vinegars are used, residual fermentative microbes promotes aging action (enzyme reactions: fermentation and maturation) and their value will be increased, when they are treated as foods and drinks, and furthermore, nourishments (nutritional supplements) and *Gnetum* extract, and further seasonings without processing.

And the alcohol concentration of the aqueous ethanol solution is 15% or higher, preferably between 20% and 70%, and more suitably between 30% and 50%. When the alcohol concentration is excessively low, the extractive efficiency is too low. When the alcohol concentration is excessively high, there is little hope for further increase of extractive efficiency.

The usage of alcohol solution (aqueous extractant) varies depending upon the alcohol concentrations, etc., but should exceed the amount in which *Gnetum* material (material for extraction) can be sufficiently steeped. For example, the alcohol solution should be added 1 to 20 parts, preferably 2 to 10 parts for one part of *Gnetum* seeds. When the alcohol solution is added excessively, it costs the time to distill away solvents (extractant), which is not desirable.

In the present invention, the extractable material (*Gnetum* extract) separated from the above-mentioned material for extraction shall indicate the absorption maximum in the neighborhood of 320 nm in ultraviolet region when the absorption spectrum is measured in aqueous 50% ethanol solution and shall have a thin-layer chromatogram that shows the spot in the neighborhood of Rf value 0.5 by thin-layer chromatography developing in chloroform-methanol mixed solution (volume ratio 4:1) on silica gel used as a carrier. This is to confirm the existence of active ingredients which indicate antimicrobial action and antioxidative effect of the extractable material of *Gnetum* and to investigate losses in process of the treatment and manufacture of the material.

The extraction time is a key to the extraction of the useful ingredient from the seeds, and aging for more than 12 hours is desirable. In this case, aging means to primarily enable enzymes in *Gnetum* seeds to thoroughly function. The main useful ingredients in the aged *Gnetum* extract include Gnetin C, Gnemonocide A, Gnemonocide C, and Gnemonocide D which have been identified by spectral analysis. The antimicrobial action decreases in order of Gnetin C>Gnemonocide C≈Gnemonocide D, and Gnemonocide A does not show the antimicrobial action. The antimicrobial action of Gnetin C is not dependent on pH from the acidic region to alkaline region. Especially, the merit is that the antimicrobial action is exhibited even in the neutral region, where other antimicrobial substances are no effect. The scavenging radical action (antioxidative effect) to 1,1-diphenyl-2-picrylhydrazyl (hereinafter called "DPPH") decreases in order of Gnetin C>Gnemonocide C≈Gnemonocide D>Gnemonocide A. The spot in the neighborhood of Rf value 0.5 by thin-layer chromatography (abbreviated as "TLC") developing in a mixture of chloroform-methanol (4:1, v/v) corresponds to Gnetin C and the spot in the neighborhood of Rf value 0.15 by TLC with a mixture of chloroform-methanol (2:1, v/v) as the developing solvent corresponds to Gnemonocide A. These four compounds are polyphenol which belongs to stilbenoid.

The material containing *Gnetum* extract and *Gnetum* extract according to the present invention can be manufactured as follows: Under the condition where the *Gnetum* seeds (fruits) (material for extracting) are completely soaked (immersed) in the said aqueous extractant, at room temperature with stirring, if required, and by heating (up to about 70° C.) if required, the ingredients (extractable material) are eluted (leached) with being aged (enzyme-reacted).

And in the case producing extract, the soaking solution is filtered to remove insoluble matters and then the filtrate is concentrated at atmospheric pressure or under reduced pressure to obtain the concentrate (extract) distilled away the solvent or is freeze-dried or spray-dried to obtain the extractable material (both are called "*Gnetum* extract.")

Suitably, in accordance with the desired preparation form, to the extract (filtrate), it is possible to add the following:
1) Inclusion agents, such as alpha-, beta- and gamma-cyclodextrin, diverged (or branched) cyclodextrin, etc.;

2) Excipients, such as dextrin, oligosaccharide, and other water-soluble sugars, acetic acid, ascorbic acid, citric acid, and other organic acids and their salts, glycine; monosodium glutamate, and other amino acids; potassium phosphate, sodium sulfate, and other inorganic salts, etc.; and
3) Surfactants, such as glycerol fatty acid ester, sodium alkyl sulfate, sucrose fatty acid ester, sorbitan fatty acid ester, lecithin, saponin, yucca extracts, etc.

By the way, the extract (concentrate) can be further purified by silica gel column chromatography, reversed phase column chromatography, gel filtration chromatography, etc.

Heat treatment of the present invention is to bring the immersion liquid temperature to be higher than room temperature, preferably to temperature higher than 30° C., and more suitably, means an operation (process) to immerse (soak) the material for extraction in an immersion liquid at a temperature between 30 and 60° C. where enzymes function satisfactorily.

The *Gnetum* extract of the present invention can be mixed with food additives in foods, such as other essences and extracts, seasonings (including soy sauce, miso, sauces, etc.), acidulant, sweetener, flavoring substance, coloring agent, preservatives, fortification agent, thickening agent, emulsifier, quality improving agent, etc. And, in cosmetics and hygienic goods, other extracts, excipients, emulsifier, solution adjuvant, pH adjuster, thickening agents, perfume, etc. may be blended.

Reading the present invention, *Gnetum* extract manufactured from *Gnetum* seeds which are constantly eaten in Southeast Asia is safe, and has antimicrobial action and free radical scavenging action (antioxidative effect), *Gnetum* extract can be used safely not only for eatables and drinkables and food and drink for pets but also for various fields such as clothes, hygienic products, etc.

For example, *Gnetum* extract can be used as an agent prolonging shelf life (antimicrobial agent) of various processed foods and health-improving ingredients in functional foods (healthy foods).

As health-improving functions, various preventive functions to diseases such as heart disease, encephalopathy, atherosclerosis, cancer, collagen disease (rheumatosis etc.), glaucoma, Alzheimer disease, etc., inflammation caused by sunburns, and suppression of melanin synthesis (whitening effect), hair growing and hair loss prevention, promotion of curing of wounds as hygienic products, etc., and deodorizing sanitary products, etc. are expected.

Furthermore, it has been found that *Gnetum* extract of the present invention can be used as food additives which not only masks grassy-smell, acridity (harsh taste), and astringency, by mixing with vegetable extract prepared in the same manner as *Gnetum* extract or vegetable juice such as green juice, etc. but also imparts flavor and full body (richness) to foods.

The vegetables includes "Ashitaba (*Angelica keiskei*)," asparagus, oilseed rape, avocado, peas, barley, okra, pumpkin, cauliflower, cabbage, cucumber, "Komatsuna (*Brassica rapa* L. var. *pervidis* Bailey)," garland chrysanthemum, "Seri (Japanese parsley)," celery, Japanese radish, onion, "qing-geng-cai (*Brassica chinensis*)", tomato, eggplant, carrot, Chinese cabbage, spinach, Jews mallow (*Corchorus olitorius*), "Yosai (*Ipomoea aquatica* Forsk)," mugwort, lettuce, lotus root, guava, burdock, beet, broccoli, parsley, green pepper, etc. And one kind of them or two or more kinds of them in combination can be used for extraction. The vegetables are preferable either as it is (raw) or in a dry state.

By the way, the vegetable extract can be manufactured in the same manner as *Gnetum* extract.

That is, after the vegetables are washed and with or without being comminuted, the said aqueous extractant is added to the vegetables in more than an amount that is enough to nearly completely immerse vegetables with the water content exuding from vegetables taken into account, and at room temperature or with heating (less than about 70° C.), with stirring as required (in the case that vegetables are added without being ground, use a cutting blade instead of the stirring paddle), extracting operation is carried out for a stated time (for example, 1 to 12 hours). And from the solid-liquid mixture obtained by extracting treatment in this way, operation by separation such as filtration, etc. of solid-liquid is carried out to obtain extracted liquid (extract). And from the relevant extracted liquid, solvents are distilled away at atmospheric pressure or under reduced pressure to produce a concentrated liquid or vegetable extract is obtained in the form of powders or other solids by freeze-drying or spray-drying.

In such case, in accordance with the target preparation form, in the same manner as the above-mentioned *Gnetum* extract, inclusion agent, excipient, and surfactant are added to the extracted liquid.

By the way, the above-mentioned vegetable extraction operation may be carried out simultaneously on *Gnetum* seed material and vegetables in the same extraction container.

And the addition amount (mixture amount) of *Gnetum* extract to 100 parts of vegetable extract varies in accord with the purity of *Gnetum* extract, but should be 1 to 100 parts. Excessively small amount of *Gnetum* extract cannot exhibit mask effect of bad taste (disagreeable taste, undesirable taste) such as grassy-smell, raw-fishy smell, acridity, and astringency of vegetable extract when adding to the foods, and excessively large amount of *Gnetum* extract weakens flavor of vegetable, which is not preferable.

Needless to say, the vegetable extract of the present invention may be mixed with food additives, such as seasoning, acidulant, sweetener, flavoring substance, coloring agent, preservatives, fortification agent, thickening agent, emulsifier, quality improving agent, manufacturing agent etc. to formulate products.

BEST MODE FOR CARRYING OUT THE INVENTION

Figure 1:
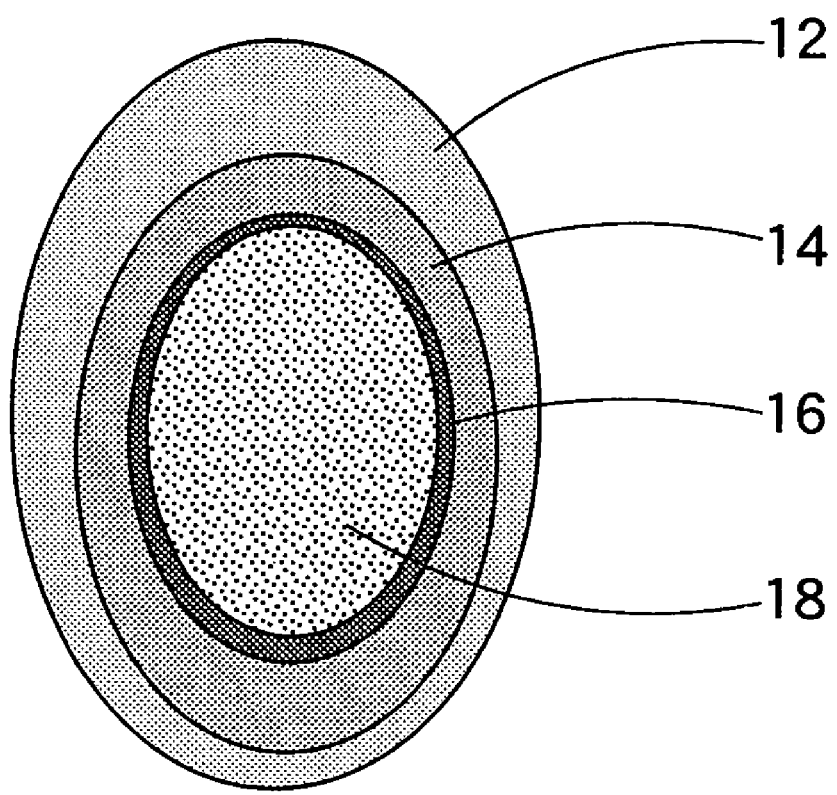
FIG. 1 is a model cross-sectional view of *Gnetum* fruit.

Now, the present invention will be described in detail as follows using embodiments, comparison examples, and in addition, applied examples.

*Gnetum* fruit used in each embodiment is of a dry form prepared by drying in the sun and has about 10% mean weight loss on drying. In addition, Emping Belinjo is in the state before being fried in oil or sautéed with oil, flattening after heating semi-dried seeds, and drying in shade as described above, and those produced by P. T. SEKAR ALAM, Indonesia were used.

And crushed products of *Gnetum* fruit or seeds used in each embodiment and comparison example were prepared as described below.

1) *Gnetum* fruit slices: Undried *Gnetum* fruit is sliced into about 1 mm thick with cooking cutter.
2) *Gnetum* seed slices: Epicarp of *Gnetum* fruit is peeled and *Gnetum* seed with seed coat and thin coat left is sliced into about 1 mm thick with cooking cutter.

3) *Gnetum* fruit products ground: Dried *Gnetum* fruit is medium-ground (particle size: about 0.5 to 3 mm) as it is with coffee mill.

4) *Gnetum* seeds with the skin products ground . . . . Seeds (with seed skin and thin skin left) obtained by peeling epicarp from dry *Gnetum* fruit is medium-ground (particle size: about 0.5 to 3 mm) with coffee mill.

5) Peeled *Gnetum* seed products ground: From dry *Gnetum* fruit, epicarp, seed skin and thin skin are peeled and the peeled seed is medium-ground (particle size: about 0.5 to 3 mm) with coffee mill.

A. EMBODIMENT GROUP I

Embodiment I-1

One kilogram of methanol was added to 100 g of *Gnetum* fruit slices and heated and refluxed for 3 hours, and then, filtered. The filtrate was concentrated and evaporated under vacuum to obtain 3.2 g of candy-like *Gnetum* extract.

When absorption spectrum of the *Gnetum* extract was measured in 50% ethanol solution, the absorption maximum was indicated at 315 nm, and when thin-layer chromatography (silica gel TLC; developing solvent: chloroform/methanol=4/1) was carried out, the spot was indicated at Rf value 0.45.

Embodiment I-2

334 g of *Gnetum* seed slices was immersed in 900 g of 50% ethanol at room temperature and then, filtered. The filtrate was vacuum-concentrated to distill away ethanol; then, the concentrate was freeze-dried to obtain 22.5 g of solid (powdered) *Gnetum* extract. When they were analyzed in the same manner as Embodiment I-1 the absorption maximum was indicated at 320 nm and the spot was indicated at Rf value 0.50.

Embodiment I-3

246 g of ground products of peeled *Gnetum* seed was immersed in 3 kg of 30% ethanol for 3 hours at about 50° C. and then, filtered. The filtrate is vacuum-concentrated to distill away ethanol, and 25 g of glycerol fatty acid ester and 50 g of dextrin were dissolved in the concentrate, and spray-dried to obtain 101.1 g of powdered *Gnetum* extract. When the *Gnetum* extract was analyzed in the same manner as Embodiment I-1, the absorption maximum was indicated at 325 nm and the spot was indicated at Rf value 0.55.

Embodiment I-4

350 g of ground product of peeled *Gnetum* seed was immersed in 4 kg of water at room temperature for 3 days, and then, filtered. To the filtrate, 30 g of beta-cyclodextrin was added, stirred for 30 minutes, and vacuum-concentrated; then spray-dried to obtain 55.2 g of powdered *Gnetum* extract. When the *Gnetum* extract was analyzed in the same manner as Embodiment 1, the maximum absorption was indicated at 313 nm and the spot was indicated at Rf value 0.48. When the total nitrogen amount was measured by the Kjeldahl method, it was 2.9 g/100 g.

By the way, 3 parts of the present *Gnetum* extract, 10 parts of cut *Flammulina veluptipes*, and 30 parts of diced tofu were added to 300 parts of water and heated, and when they were boiled, 5 parts of finely cut long green onion and 30 parts of miso were added to prepare miso soup. The miso soup was endowed with full body. On the other hand, miso soup to which no *Gnetum* extract was added tasted light only with miso.

Embodiment I-5

One-hundred grams of *Gnetum* fruit slices was immersed in 500 mL of acetone for 5 days at room temperature, and then, filtered. The filtrate was vacuum-concentrated and 1.7 g of liquid (oily) *Gnetum* extract was obtained. When the *Gnetum* extract was analyzed in the same manner as Embodiment 1, the maximum absorption was indicated at 313 nm and the spot was indicated at Rf value 0.47.

By the way, for samples of lard with 0.05% of the present *Gnetum* extract added and with no extract added, the induction period (time to point of inflexion where conductivity greatly changes) was measured by CDM (conductometric determination method; temperature: 120° C.; air content: 20 L/h). As a result, the induction period was 0.15 hours for the sample with no extract added, whereas it was 3.02 hours for the sample with extract added, indicating that the present *Gnetum* extract exhibited marked lipid peroxidation suppressing effect.

Comparison I

Ninety-one grams of Emping Belinjo (available from P. T. SEKAR ALAM, Indonesia) was immersed in 900 g of 50% ethanol at room temperature for 2 days and, then, filtered. The filtrate was concentrated and evaporated under vacuum, and 8.2 g of syrup Emping extract was obtained. When it was analyzed in the same manner as Embodiment 1, the maximum absorption was indicated at 302 nm but no spot was found in the neighborhood of Rf value 0.5.

The minimum growth inhibition concentrations (MIC) of the *Gnetum* extract obtained in each embodiment were 0.01 to 0.1% against hay *bacillus* (*Bacillus subtilis*), 0.1 to 0.2% against *Escherichia coli*, 0.1 to 0.2% against sake yeast (*Saccharomyces cerevisiae*), and 0.2 to 0.4% against *penicillium* (*Penicillium expansum*) without being susceptible not only to sugar, protein, and lipid but also to pH between pH 3 and pH 9 and exhibited antimicrobial effect, but no antimicrobial effect was recognized in Emping Belinjo for comparison I.

When the DPPH radical scavenging effect was examined for each of 0.02% solution of *Gnetum* extract obtained in Embodiment I-2 and Emping extract obtained in Comparison I, the radical scavenging effect of *Gnetum* extract was 2.9 times that of Emping extract.

Cosmetic-Applied Example 1

Lotion

A solution in which 1 part of *Gnetum* extract of Embodiment I-2, 9 parts of polyoxyethylene (20) lauryl ether, 0.5 part of methyl parahydroxybenzoate and a suitable amount of perfume were dissolved in 100 parts of ethanol was added with stirring to an aqueous solution in which 50 parts of glycerol and 40 parts of 1,3-butylene glycol were added to 780 parts of purified water, dissolved, and then, 19.5 parts of purified water were added to produce lotion.

Cosmetic-Applied Example 2

Skin Cream

A composition comprising 2 parts of *Gnetum* extract of Embodiment I-4, 5.5 parts of squalan, 3 parts of olive oil, 2 parts of stearic acid, 2 parts of yellow bees wax, 3.5 parts of octyldodecyl myristate, 3 parts of polyoxyethylene (20) cetyl ether, 1.5 parts of behenyl alcohol and 2.5 parts of glycerol monostearate was heated to 70° C. and dissolved to mix, and separately, an aqueous solution in which 8.5 parts of 1,3-butylene glycol, 0.2 part of methyl parahydroxybenzoate and 0.03 part of butyl parahydroxybenzoate were stirred and dissolved in 67 parts of purified water at 80° C. and a suitable amount of perfume were added with stirring to emulsify and produce skin cream.

Cosmetic-Applied Example 3

Skin Milk

A composition comprising 1 part of *Gnetum* extract of Embodiment I-4, 0.5 part of mangosteen extract, 5.5 parts of Squalan, 5 parts of olive oil, 5 parts of Johoba oil, 1.5 parts of cetyl alcohol, 2 parts of glycelol monostearate, 3 parts of polyoxyethylene (20) cetyl ether, and 2 parts of polyoxyethylene (20) sorbitan monooleate was heated to 70° C. and dissolved to mix, and separately, an aqueous solution in which 1 part of dipropylene glycol, 2 parts of glycerol, and 0.2 part of methyl parahydroxybenzoate were stirred and dissolved in 72 parts of purified water at 80° C. and a suitable amount of perfume were added with stirring to emulsify and further cooled with stirring to produce skin milk.

By the way, the above-mentioned mangosteen extract was an extract prepared by the following method.

To 84 g of medium-ground substance of mangosteen dried epicarp (particle size: 0.5 to 3 mm), 860 mL of 60% ethanol was added and stirred at 60° C. for 3 hours, and then, filtered. And the filtrate was vacuum-concentrated to distill away ethanol and freeze-dried and 21 g of pale-brown mangosteen extract was obtained.

B. EMBODIMENT GROUP II

Comparison II-1

After 100 g of ground products of peeled *Gnetum* seed was added to 300 mL of 99% ethanol and agitated for 2 days, the insoluble matter was filtered and fluid *Gnetum* seed extract was obtained. This fluid extract was vacuum-concentrated and 4.8 g of candy-like (thick malt syrup form) *Gnetum* extract was obtained. When the obtained *Gnetum* extract was examined by TLC, both spots in the neighborhood of Rf value 0.15 (developing solvent: chloroform/methanol=2/1) and 0.5 (developing solvent: chloroform/methanol=4/1) were faintly recognized. That is, it indicates that with alcohol only, it is difficult to obtain the desired extractable material.

Comparison II-22

After 200 g of ground products of peeled *Gnetum* seed was added to 600 mL of 99% ethanol and heated and refluxed for 5 hours with stirring, the insoluble matter was filtered off and *Gnetum* seed extract liquid was obtained. This *Gnetum* extract liquid was vacuum-concentrated and 13.8 g of thick malt syrup form *Gnetum* extract was obtained. When the obtained *Gnetum* extract was examined by TLC, the spot at Rf value 0.15 (developing solvent: chloroform/methanol=2/1) was able to be recognized but the spot in the neighborhood of Rf value 0.5 (developing solvent: chloroform/methanol=4/1) was faintly recognized. That is, it indicates that with alcohol only, it is difficult to obtain the desired extractable material.

Embodiment II-1

After 100 g of ground products of peeled *Gnetum* seed was added to 500 g of 16% ethanol and agitated overnight, the insoluble matter was filtered and *Gnetum* seed extract liquid was obtained. This *Gnetum* extract liquid was vacuum-concentrated and 10.1 g of thick malt syrup form *Gnetum* extract was obtained. When the obtained *Gnetum* extract was examined by TLC, the spot at Rf value 0.15 (developing solvent: chloroform/methanol=2/1) and the spot in the neighborhood of Rf value 0.5 (developing solvent: chloroform/methanol=4/1) were recognized at the same level.

By the way, one example of the composition when seasoning using the present *Gnetum* extract is formulated is described as follows.

*Gnetum* extract: 1 part; monosodium glutamate: 5 parts; glycine: 3 parts; sodium citrate: 1 part Embodiment II-2

After 50 g of ground products of peeled *Gnetum* seed was immersed in 300 g of 40% ethanol for one day, it was stirred for 5 hours at 50° C., the insoluble matter was filtered and *Gnetum* seed extract liquid was obtained. This *Gnetum* extract liquid was vacuum-concentrated and 6.8 g of thick malt syrup form *Gnetum* extract was obtained. When the obtained *Gnetum* extract was examined by TLC, the spot in the neighborhood of Rf value 0.5 (developing solvent: chloroform/methanol=4/1) was larger than the small spot in the neighborhood of Rf value 0.15 (developing solvent: chloroform/methanol=2/1).

Embodiment II-3

After 500 g of ground products of peeled *Gnetum* seed was immersed in 2 kg of 60% ethanol for 7 days, the insoluble matter was filtered and *Gnetum* seed extract liquid was obtained. This *Gnetum* extract liquid was vacuum-concentrated and 55 g of thick malt syrup form *Gnetum* extract was obtained. When the obtained *Gnetum* seed extract was examined by TLC, the spot in the neighborhood of Rf value 0.15 (developing solvent: chloroform/methanol=2/1) was scarcely recognized, whereas the spot in the neighborhood of Rf value 0.5 (developing solvent: chloroform/methanol=4/1) was large.

Embodiment II-4

After 200 g of ground products of peeled *Gnetum* seed was immersed in 2 kg of 80% acetone overnight, it was stirred for 5 hours at 60° C. and for 3 days at room temperature, the insoluble matter was filtered and *Gnetum* seed extract liquid was obtained. This *Gnetum* extract liquid was vacuum-concentrated and 18.6 g of thick malt syrup form *Gnetum* extract was obtained. When the obtained *Gnetum* extract was examined by TLC, the spot in the neighborhood of Rf value 0.15 (developing solvent: chloroform/methanol=2/1) was slightly recognized, whereas the spot in the neighborhood of Rf value 0.5 (developing solvent: chloroform/methanol=4/1) was large.

Embodiment II-5

After 1 kg of ground products of peeled *Gnetum* seed were immersed in 3 kg of 50% methanol for 5 days, the insoluble matter was filtered and *Gnetum* seed extract liquid was obtained. This *Gnetum* extract liquid was vacuum-concentrated and 11.3 g of thick malt syrup form *Gnetum* extract was obtained. When the obtained *Gnetum* extract was examined by TLC, the spot in the neighborhood of Rf value 0.15 (developing solvent: chloroform/methanol=2/1) was scarcely recognized, whereas the spot in the neighborhood of Rf value 0.5 (developing solvent: chloroform/methanol=4/1) was large.

Embodiment II-6

After 150 g of *Gnetum* fruit slices was added to 1.5 kg of methanol and stirred for 10 hours at 40° C., the insoluble matter was filtered and *Gnetum* extract liquid was obtained. This *Gnetum* extract liquid was vacuum-concentrated and 4.9 g of thick malt syrup form *Gnetum* extract was obtained. When the obtained *Gnetum* extract was examined by TLC, the spot at Rf value 0.15 (developing solvent: chloroform/methanol=2/1) and the spot in the neighborhood of Rf value 0.5 (developing solvent: chloroform/methanol=4/1) were recognized at the same level.

Embodiment II-7

Fifty five grams of Emping were immersed in 500 g of 50% ethanol for 2 days at room temperature, and then filtered. To this filtrate, 20 g of the insoluble matter filtered off in Embodiment II-3 were added and stirred for 2 days at room temperature; the insoluble matter was filtered and Emping extract liquid (material containing *Gnetum* extract) was obtained. This extract liquid was vacuum-concentrated and 5.1 g of thick malt syrup form *Gnetum* extract was obtained. When the obtained *Gnetum* extract was examined by TLC, the spot in the neighborhood of Rf value 0.15 (developing solvent: chloroform/methanol=2/1) was able to be faintly recognized only, whereas the spot in the neighborhood of Rf value 0.5 (developing solvent: chloroform/methanol=4/1) was large.

Embodiment II-8

246 g of ground products of peeled *Gnetum* seed was immersed in 3 kg of 30% ethanol for 3 hours at 50° C. and filtered. The filtrate was vacuum-concentrated to distill away ethanol; then, 25 g of glycerol fatty acid ester and 50 g of cyclodextrin (Isoelite P available from Ensuiko Sugar Refining Co., Ltd.) were dissolved in the concentrate; then, it was spray-dried and 101.1 g of powdered *Gnetum* extract was obtained. When the obtained *Gnetum* extract was examined by TLC, the spot in the neighborhood of Rf value 0.5 (developing solvent: chloroform/methanol=4/1) was slightly smaller than the spot in the neighborhood of Rf value 0.15 (developing solvent: chloroform/methanol=2/1).

Embodiment II-9

After 350 g of ground products of peeled *Gnetum* seed was immersed in 4 kg of 40% ethanol for 3 days at room temperature, the insoluble matter was filtered and *Gnetum* seed extract liquid was obtained. To this extract liquid, 30 g of beta-cyclodextrin was added, agitated for 30 minutes, and vacuum-concentrated; then, it was spray-dried and 55.2 g of powdered *Gnetum* extract was obtained. When the obtained *Gnetum* extract was examined by TLC, the spot in the neighborhood of Rf value 0.15 (developing solvent: chloroform/methanol=2/1) was faintly recognized, whereas the spot in the neighborhood of Rf value 0.5 (developing solvent: chloroform/methanol=4/1) was large.

Test Example I (1) The minimum growth inhibition concentrations of the *Gnetum* extract obtained in each embodiment of Embodiment group II-1 through 9 were between 0.01% and 0.1% against hay *bacillus*, between 0.1% and 0.2% against *Escherichia coli*, between 0.1% and 0.2% against sake yeast, and between 0.2% and 0.4% against *penicillium* and antimicrobial effect was exhibited, but no antimicrobial effect was recognized in *Gnetum* extract of Comparison II-1 and 2.

(2) When the DPPH radical scavenging effect was examined for each of 0.02% solution of *Gnetum* extract obtained in Embodiment II-3 and *Gnetum* extract obtained in Comparison II-1, the radical scavenging effect of *Gnetum* extract of Embodiment was 3.3 times that of Comparison.

Embodiment II-10

After 150 g of ground products of peeled *Gnetum* seed was added to the mixture water-based extractant (concentration 50%) of 300 g of water and 300 g of ethyl acetate in which 9 g of glycerol fatty acid ester (Poem J0021 available from Riken Vitamin) was dissolved and stirred overnight, the insoluble matter was filtered and liquid-form *Gnetum* extract was obtained. This extract liquid was vacuum-concentrated and 16.4 g of thick malt syrup form *Gnetum* extract was obtained. When the obtained *Gnetum* extract was examined by TLC, the spot at Rf value 0.15 (developing solvent: chloroform/methanol=2/1) and the spot in the neighborhood of Rf value 0.5 (developing solvent: chloroform/methanol=4/1) were recognized at the same level.

Embodiment II-11

After 300 g of ground products of peeled *Gnetum* seed was added to 900 g of mixture 20% ethanol in which 6 g of yucca extract (SARAKEEP PE available from Maruzen Pharmaceuticals Co., Ltd.) was dissolved and stirred for 2 days, the insoluble matter was filtered and liquid-form *Gnetum* extract was obtained. This extract liquid was vacuum-concentrated and 39.3 g of thick malt syrup form *Gnetum* extract was obtained. When the obtained *Gnetum* extract was examined by TLC, the spot in the neighborhood of Rf value 0.5 (developing solvent: chloroform/methanol=4/1) was slightly larger than the spot at Rf value 0.15 (developing solvent: chloroform/methanol=2/1).

Embodiment II-12

One hundred grams of ground products of peeled *Gnetum* seed (seeds roasted at 100° C.) and 0.15 g of beta-glucosidase of almond (available from Fluka Company) were added to a mixed solution (about 22%) of 280 g of water and 100 g of ethanol and stirred for 2 days at 35° C., the insoluble matter was filtered and liquid-from *Gnetum* extract was obtained. This extract liquid was vacuum-concentrated and 10.6 g of thick malt syrup form *Gnetum* extract was obtained. When the obtained *Gnetum* extract was examined by TLC, the spot in the neighborhood of Rf value 0.15 (developing solvent: chloroform/methanol=2/1) was faintly recognized, whereas the spot in the neighborhood of Rf value 0.5 (developing solvent: chloroform/methanol=4/1) was large.

Embodiment II-13

After 200 g of ground products of peeled *Gnetum* seed was immersed in 800 g of 20% acetic acid for 3 days at room temperature, the insoluble matter was filtered and liquid-form *Gnetum* extract was obtained. This extract liquid was freeze-dried and 18.3 g of powder form *Gnetum* extract was obtained. When the obtained *Gnetum* extract was examined by TLC, the spot at Rf value 0.15 (developing solvent: chloroform/methanol=2/1) and the spot in the neighborhood of Rf value 0.5 (developing solvent: chloroform/methanol=4/1) were recognized at the same level.

Test Example II

Examples of tests carried out to confirm the antioxidative action of each embodiment will be described as follows.

As samples, with respect to each *Gnetum* extract and Emping extract obtained in above-mentioned Embodiment I-2, Embodiment II-3, Comparison I and Comparison II-1, and the mangosteen extract prepared in cosmetic-applied example 3, as well as a mixture of equal part of Embodiment II-3 and mangosteen extract, 2 mL of 50% ethanol solution containing 0.02 mg each of them was added to 2 mL of 0.1M acetic acid buffer solution (pH 5.5), to which 1 mL of 0.2 mM DPPH ethanol solution was added. After 6 hours, decreases of absorbance (absorbance difference) at 517 nm of these reaction solutions were measured.

The results are as shown in Table 1, and a decrease of absorbance (absorbance difference) based on DPPH radical is 2.9 times that of the Emping extract of Comparison I in the *Gnetum* extract of Embodiment I-2 and 3.3 times of *Gnetum* extract of Comparison II-1 in the *Gnetum* extract of Embodiment II-3. Based on this, it has been confirmed that the DPPH radical scavenging action (antioxidative action) of the *Gnetum* extract of the present invention is improved in proportion to the size of the spot in the neighborhood of Rf value 0.5. In addition, it has been able to be confirmed that the *Gnetum* extract of Embodiment II-3 synergistically increases the antioxidative action by the combined use of mangosteen extract.

TABLE 1

| Sample | Absorbance | Absorbance difference |
| --- | --- | --- |
| Control | 0.557 | — |
| Embodiment I-2 | 0.397 | 0.160 |
| Comparison I | 0.502 | 0.055 |
| Embodiment II-3 | 0.296 | 0.261 |
| Comparison II-1 | 0.478 | 0.079 |
| Mangosteen extract | 0.337 | 0.220 |
| Embodiment II-3 + mangosteen extract | 0.154 | 0.403 |

*Control: 50% ethanol containing no sample was added.
Absorbance difference: (absorbance of control) − (absorbance of sample)

C. EMBODIMENT GROUP III

Embodiment III-1

To 1 kg of undried *angelica*, 1 kg of 20% ethanol was added, stirred and comminuted by mixer, immersed for one day at room temperature, and filtered, and the solvent was distilled away under reduced pressure, and 22 g of liquid *angelica* extract was obtained. To 300 g of *Gnetum* fruit slices, 900 g of 50% ethanol was added, and the mixture was stirred for 20 hours at 50° C. and filtered, and from the filtrate, the solvent was distilled away under reduced pressure, and 21 g of *Gnetum* extract was obtained. Both extracts were thoroughly mixed and vegetable extract was obtained. The present vegetable extract was free of grassy smell and had the remaining flavor specific of *angelica*.

Embodiment III-2

To 3 kg of cut tomatoes, 2 kg of 50% ethanol was added and stirred for 6 hours at room temperature, the filtrate was vacuum-concentrated, and 430 g of tomato extract was obtained. One kg of product peeled and ground *Gnetum* seed was immersed in 5 kg of 10% ethanol for 2 days at room temperature and filtered, and the filtrate was vacuum-concentrated, and 295 g of *Gnetum* extract was obtained. Both extracts were mixed and vegetable extract was obtained. The present vegetable extract was free of grassy smell and tasted fruity with the acidity and the sweetness combined.

Embodiment III-3

To 800 g of undried spinach shredded with cooking cutter and 100 g of pulverized *Gnetum* fruit, 2 kg of 60% ethanol was added, agitated for 2 days at room temperature, and filtered, the filtrate was vacuum-concentrated, and 135 g of vegetable extract was obtained. The present vegetable extract was free of grassy smell and acridity (harsh taste), and had sweetness and flavor specific to spinach.

Embodiment III-4

To 200 g of dried carrot shredded with food mixer and 30 g of peeled *Gnetum* seed pulverized product, 1 kg of 40% ethanol was added and immersed for 4 days at 40° C., and then, filtered, and to the filtrate, 30 g of dextrin (Cluster Dextrin available from Ezaki Glico Co., Ltd.) was added and vacuum-concentrated, and a liquid-form *Gnetum*-carrot mixture extract was obtained. This liquid-form mixture extract was freeze-dried and 52 g of vegetable extract was obtained. This vegetable extract was free of bad taste and dry smell and possessed sweetness and flavor specific to carrots.

Comparison III-1

To 300 g of dried carrot shredded by food mixer, 1 kg of 40% ethanol was added and immersed for 4 days at 40° C., and then, filtered, and to the filtrate, 30 g of dextrin (Cluster Dextrin available from Ezaki Glico Co., Ltd.) was added and vacuum-concentrated. The concentrate was freeze-dried and 59 g of vegetable extract was obtained. The present vegetable extract possessed smell and bad taste specific to carrot.

Embodiment III-5

To a mixture of 4 parts of young barleycorn leaf powders and 1 part of vegetable extract of Embodiment III-1, 80 parts of water were added and vegetable juice was prepared. This prepared juice had lost raw fishy smell and grassy smell specific to young leaves, possessed full body and got very soft and pleasant to drink.

Embodiment III-6

To a solution dissolved 3 part of vegetable extract of Embodiment III-4, 2 parts of salt, 0.2 part of yeast extract, 0.3 part of beef extract, 0.3 part of chicken extract, and 0.2 part of amino acid seasoning in 300 parts of water, 40 parts of sliced onion were added and heated for 5 minutes to prepare onion soup. The prepared soup was free of bad tastes such as fishy smell, harsh taste, etc. resulting from onion, yeast extract, beef extract, and chicken extract, had full body (richness), and tasted nice. On the other hand, onion soup prepared by using the same amount of the vegetable extract of Comparison 4 in place of the vegetable extract of Embodiment 4 was poor-seasoned, had fishy smell and harsh taste, too, and was not enjoyable.

The invention claimed is:

1. A *Gnetum* extract comprising an aqueous extract of *Gnetum* gnemon seeds containing stilbenoid with antimicrobial and antioxidative activity, the extract made by the process comprising:

drying *Gnetum* gnemon seeds at not higher than 100° C. without converting starch in the seeds into alpha-starch; and then extracting by soaking and aging in 15 to 80% polar organic solvent below about 70° C.

2. The *Gnetum* extract according to claim 1, wherein a solution of *Gnetum* extract in 50% ethanol has an absorption spectrum that indicates the absorption maximum around 320 nm and also, has a thin-layer chromatogram that indicates the spot around Rf value of 0.5 arising from Gnetin C.

3. A vegetable extract comprising *Gnetum* extract according to claim 2.

4. A seasoning product comprising the *Gnetum* extract according to claim 2 as an essential ingredient.

5. A cosmetic comprising the *Gnetum* extract according to claim 1, wherein the *Gnetum* extract is the active ingredient of the cosmetic.

6. The *Gnetum* extract according to claim 1, wherein the stilbenoid is Gnetin C.

7. The cosmetic according to claim 5, wherein the stilbenoid is Gnetin C.

8. The *Gnetum* extract according to claim 1, wherein the extract is an *Gnetum* extract aged for more than 12 hours.

9. The *Gnetum* extract according to claim 1, wherein the seeds, prior to extraction, are processed to remove a pericarp and a seed coat leaving an endosperm portion of the seed.

10. The *Gnetum* extract according to claim 1, wherein an extractant is an aqueous ethanol solution.

11. The *Gnetum* extract according to claim 1, wherein an extractant is an aqueous ethanol solution between 20% and 70%.

12. The *Gnetum* extract according to claim 1, wherein the *Gnetum* extract is obtained by filtering and then distilling away the solvent.

\* \* \* \* \*